United States Patent
Milpied et al.

(10) Patent No.: US 8,855,764 B2
(45) Date of Patent: Oct. 7, 2014

(54) SYSTEM AND METHOD FOR DETECTING ATRIAL ACTIVITY SIGNAL USING A MONOBODY LEAD IN A SINGLE CHAMBER IMPLANTABLE CARDIOVERTER/DEFIBRILLATOR

(75) Inventors: Paola Milpied, Paris (FR); Christine Henry, Paris (FR)

(73) Assignee: Sorin CRM S.A.S., Clamart Cedex (FR)

( * ) Notice: Subject to any disclaimer, the term of this patent is extended or adjusted under 35 U.S.C. 154(b) by 460 days.

(21) Appl. No.: 12/966,830

(22) Filed: Dec. 13, 2010

(65) Prior Publication Data

US 2011/0144705 A1   Jun. 16, 2011

(30) Foreign Application Priority Data

Dec. 11, 2009   (FR) .................................... 09 58898

(51) Int. Cl.
| | | |
|---|---|---|
| *A61N 1/362* | (2006.01) | |
| *A61N 1/39* | (2006.01) | |
| *A61N 1/38* | (2006.01) | |
| *A61N 1/365* | (2006.01) | |
| *A61N 1/368* | (2006.01) | |
| *A61B 5/0464* | (2006.01) | |

(52) U.S. Cl.
CPC ............ *A61N 1/3962* (2013.01); *A61B 5/0464* (2013.01)
USPC ..................... 607/18; 607/4; 607/5

(58) Field of Classification Search
USPC .................................. 607/4, 5, 18
See application file for complete search history.

(56) References Cited

U.S. PATENT DOCUMENTS

| | | |
|---|---|---|
| 4,643,201 A | 2/1987 | Stokes |
| 5,462,060 A | 10/1995 | Jacobson et al. |
| 5,628,779 A | 5/1997 | Bornzin et al. |
| 5,776,072 A | 7/1998 | Hsu et al. |
| 5,776,165 A | 7/1998 | Ripart |
| 5,782,876 A | 7/1998 | Flammang |
| 5,868,793 A | 2/1999 | Nitzsche et al. |
| 5,885,221 A | 3/1999 | Hsu et al. |
| 5,891,170 A | 4/1999 | Nitzsche et al. |
| 6,321,122 B1 | 11/2001 | Scheiner et al. |
| 6,636,770 B2 | 10/2003 | Ripart |
| 6,760,619 B1 * | 7/2004 | Helland et al. ............... 607/4 |
| 6,889,080 B2 | 5/2005 | Henry et al. |
| 8,095,207 B2 * | 1/2012 | Belalcazar et al. ......... 600/512 |
| 2005/0177219 A1 | 8/2005 | Ollivier et al. |

OTHER PUBLICATIONS

"Integrated Microsized Semiconductor Strain Gauge and Its Biomedical Applications," Implantable sensors for closed-loop prosthetic systems, Chapter 6, (Futura Publishing Company Inc., 1985; edited by Wen H. Ko and co-edited by Jacques Mugica & Alain Ripart).
Foreign Search Report (Annexe Au Rapport De Recherche Preliminaire Relatif A La Demande De Brevet Francais No. FR0958898 FA730423), Aug. 4, 2010.

* cited by examiner

*Primary Examiner* — Tammie K Heller
(74) *Attorney, Agent, or Firm* — Foley & Lardner LLP

(57) ABSTRACT

A single-chamber implantable device for detecting a patient's atrial activity using a monobody lead is disclosed. The monobody lead (10) includes a ventricular coil (16), a supraventricular coil (18), a distal electrode (14) forming three electrodes for detecting depolarization signals. A generator (12) of the implantable device collects a first unipolar signal (20) between the ventricular coil and the generator housing and a second unipolar signal (22) between the supraventricular coil and the generator housing. An independent component analysis is performed to the detected depolarization signals to determine an estimated atrial activity signal from the first and second unipolar signals.

20 Claims, 2 Drawing Sheets

RV COIL + HOUSING

RV COIL + HOUSING

A SOURCE

DERIVATE FROM THE A SOURCE

SYSTEM AND METHOD FOR DETECTING ATRIAL ACTIVITY SIGNAL USING A MONOBODY LEAD IN A SINGLE CHAMBER IMPLANTABLE CARDIOVERTER/DEFIBRILLATOR

The present application claims the benefit of French Application No. 09-58898 entitled "Single Chamber Implantable Cardioverter/Defibrillator With Detection Of The Atrial Activity By A Monobody Lead" and filed Dec. 11, 2009, which is hereby incorporated by reference in its entirety.

FIELD

The present invention relates to "active implantable medical devices" as defined by the 20 Jun. 1990 Directive 90/385/EEC of the Council of the European Communities, and more particularly to devices that respond to a tachyarrhythmia and deliver to the heart of a patient electrical pulses of a high energy level that significantly exceeds the energy level required for a simple cardiac stimulation.

BACKGROUND

The devices that deliver high energy electrical pulses are generally called implantable cardioverter/defibrillators, or ICDs. They generally have two principal elements, a pulse generator, and a lead or a system of leads. The pulse generator (often more simply referred to as a "generator") functions to monitor the patient's cardiac activity and generate high energy electrical pulses when the heart is determined to have a ventricular arrhythmia that may be treated by applying a shock. As defined herein, the term "shock" or "shock energy" should be understood to mean an electrical pulse of a high energy that is significantly stronger than the electrical energy used for applying conventional stimulations. Such high energy electrical pulse includes a shock for cardioversion and/or defibrillation. The lead or system of leads is connected to the generator and functions to appropriately distribute the shock energy to the patient's heart. EP 0773039 A1 and its counterpart U.S. Pat. No. 5,776,165 assigned to Sorin CRM (previously known as ELA Medical) describes an exemplary generator/lead system, and a technique for selecting an application-specific optimal configuration for delivering required shock energy.

Typically, shock energy is delivered only when it is determined that a true ventricular tachycardia (VT) exists, and not when a supra-ventricular tachycardia (SVT) exists. In the latter case, the SVT is of an atrial origin, and the shock electrode is located at the ventricle, therefore this way of shock energy delivery would be inefficient because the shock energy would be delivered to the ventricle, not to the atrial region. In addition, the application of a shock in a conscious patient is extremely painful and agonizing, because the delivered energy is well above the typical pain threshold. Furthermore, the application of a shock causes side effects on the heart rhythm as it increases a risk of developing secondary disorders, on the functional integrity of the patient's myocardium, and generally, on the patient's physiological balance.

It is therefore desirable to deliver high energy shocks only when appropriate and only if a less painful alternative therapy, such as an appropriate stimulation of the atrium, is not possible.

An analysis of the atrial activity, which implies in particular the recognition of P waves, is a fundamental basis of this technical field. A dual-chamber defibrillator includes circuits for detecting atrial heart rhythm, from which a situation of atrial fibrillation, such as an SVT, is easily detected so as to inhibit the delivery of a shock therapy to the ventricle. However, a single-chamber defibrillator does not have such circuits for detecting rapid activity of the atrium. Thus, if the ventricular rate is fast enough, the device may unavoidably deliver an unintended and inappropriate shock to the ventricle.

However, it is recognized that implementation of a single-chamber defibrillator is sufficient for patients in many cases, especially for those patients for whom a defibrillator is indicated for therapeutic treatment, but whose sinus node has no dysfunction. It should be noted that although implantation of a dual chamber defibrillator is advantageous in improving performance with regard to the classification of tachyarrhythmias (i.e., VF and SVT discrimination), it also is disadvantageous because it increases the risk of complications associated with the relatively greater number of leads and electrodes.

Implantable devices having leads to collect an atrial detection signal using a defibrillation lead are known. For example, U.S. Pat. No. 4,643,201 (assigned to Medtronic), U.S. Pat. No. 5,628,779 (assigned to Pacesetter Inc.) and U.S. Pat. No. 6,321,122 (assigned to Cardiac Pacemakers Inc.) describe various types of leads including a branch or a bend with a specific electrode that is positioned at or in the vicinity of the atrium, once the lead is implanted. EP 0801960 A2 describes another specific type of lead, with a component floating in the atrium, a bipolar electrode pair, a distal component into the ventricle and a distal electrode.

These known implantable devices, however, have relatively complex and specific leads that are not adequate for general use. On the other hand, these leads and electrodes located at the atrium float electrically delivering a relatively noisy atrial detection signal, thus making an analysis of any atrial rhythm difficult.

It is known in the art to connect a generator to a "monobody" lead, which is a single lead that contains various electrodes both to monitor the patient's heart activity and to deliver shock energy. An issue that arises with such a monobody lead is that the collection (also called the detection) of a signal representative of atrial activity is difficult because of signals for noise, e.g., muscular activity and ventricular activity that are also collected and mask the atrial activity component.

EP 1118349 A1 and its counterpart U.S. Pat. No. 6,636,770, assigned to Sorin CRM (previously known as ELA Medical), describes a monobody lead, without any ramification or bent, equipped in its proximal region with two atrial electrodes, two ventricular electrodes, and a supraventricular electrode for the delivery of a shock energy. The atrial signal is collected, on one embodiment, between the supraventricular electrode and the atrial electrode connected to it, and, on the other embodiment, between the supraventricular electrode and a second atrial electrode that is not connected to the supraventricular electrode. Even if the signal quality is improved with this lead structure, this lead structure is a non-standard model, therefore it cannot be implemented easily and widely by conventional techniques.

Other techniques have been proposed to collect atrial activity with monobody standard leads including one (or two) distal electrode(s) for monopolar detection (or bipolar detection, respectively) of a ventricular signal, a ventricular coil forming a defibrillation electrode, and a coil positioned mainly in the superior vena cava (SVC), in the vicinity of the atrium. The difficulty with this technique is that the SVC coil is not an electrode suitable for atrial detection, and it does not allow for a proper collection of atrial cardiac activity signal, especially because this electrode is electrically floating and delivering a highly noisy signal.

In particular, the atrial signal collected on the SVC coil (or more precisely, a monopolar detection between the SVC coil and the generator housing) is distorted by interference from the ventricular signal, which is often greater in amplitude than the atrial signal.

Techniques have been proposed to discriminate the atrial and ventricular components and to extract the atrial signal having a lower amplitude than the ventricular signal.

U.S. Pat. No. 5,776,072 describes one proposal in which, after signal detection and appropriate filtering, a transfer function of the ventricular channel signal compared to the signal on the combined channel (atrial+ventricular) is estimated. The estimated transfer function reflects the contribution of the R-wave to the signal on the combined channel. The application of the estimated transfer function to the signal of the combined channel provides a resultant signal that is subtracted from the signal collected on the combined channel to obtain a residual signal corresponding to an approximation of the P wave.

U.S. Pat. No. 5,885,221 (assigned to Cardiac Pacemakers Inc.) is another proposal that describes a technique, after estimating the transfer function, for calculating a convolution between the combined signal and the transfer function, thereby to obtain the contribution of the ventricular signal. This ventricular signal contribution is then removed from the combined signal to deliver an estimate of the atrial signal.

In these two prior art techniques, the discrimination between atrial and ventricular components is obtained by identifying and subtracting the R-wave signal component from a combined signal measured by a bipolar detection between the right ventricular (RV) coil electrode and the SVC coil. The calculation performed is relatively complex, and the results of these techniques have never been published. Therefore, it is unknown whether, in practice, these techniques produce a satisfactory estimate of the P wave, and whether they are clinically effective.

SUMMARY AND OBJECTS

It is therefore, an object of the present invention to collect and extract an atrial cardiac activity signal using a single-chamber defibrillator equipped with a single ventricular lead, including a standard monobody lead.

Another object of the present invention is to provide a technique for analyzing signals delivered by a conventional monobody defibrillation lead such as "double coil" (RV coil and SVC coil) standard monobody leads, and without an atrial electrode for collecting a local atrial signal.

Yet another object of the present invention is to use a "single-chamber" implantable cardioverter/defibrillator to effectively perform a "double chamber" detection from signals measured with a conventional monobody lead and detect an atrial activity signal that is sufficient for classification of tachyarrhythmias.

Broadly, the present invention is directed to collecting two unipolar signals, a first signal measured between the RV coil and the housing, and a second signal measured between the SVC coil and this housing. An Independent Component Analysis (ICA) is performed on the first and second signals to discriminate two statistically independent signals, namely an atrial activity signal and a ventricular activity signal.

One preferred embodiment of the invention is a system including an implantable device that is of a single-chamber defibrillator/cardioverter type, including a monobody lead and an implantable generator. The body of the monobody lead preferably includes: 1) a ventricular (RV) coil disposed on the patient's body and positioned in the ventricle once the lead is implanted, forming a first shock electrode for delivering a shock therapy and a first detection electrode for detecting cardiac activity (e.g., depolarization) signals; 2) a supraventricular (SVC) coil disposed on the patient's body and positioned in the superior vena cava when the lead is implanted, forming a second shock electrode for delivering a shock therapy and a second detection electrode for detecting cardiac activity (e.g., depolarization) signals, and 3) a distal electrode, preferably positioned in the ventricle when the lead is implanted, forming a third detection electrode for detecting cardiac activity (e.g., depolarization) signals.

The implantable generator preferably includes: a housing made at least in part of metal forming a reference potential electrode; circuits for analyzing signals collected by the various cardiac activity detection electrodes, including an estimator means for estimating an atrial activity signal; and circuits for delivering antitachycardia therapies including shocks.

In one embodiment, the estimator means for estimating an atrial activity signal comprises means for collecting a first unipolar signal between a ventricular (RV) coil and the generator housing; means for collecting a second unipolar signal between the supraventricular (SVC) coil and the generator housing; and means for performing an ICA analysis on the first and second unipolar signals, and determining therefrom an estimated atrial signal.

Preferably, the implantable device includes means for transforming the estimated atrial signal, after performing the ICA analysis, means for transforming said estimated atrial activity signal by a derivative operation to obtain an estimated atrial signal, means for normalizing the estimated atrial signal to a predetermined maximum absolute value, and means for applying a predetermined gain to the estimated atrial signal after normalization. It should be understood that the normalization step may be performed on the estimated atrial signal or on the transformed estimated atrial signal, as deemed appropriate.

The means for performing an ICA analysis may operate on a matrix of mixed data having a set of matrix coefficients. The matrix coefficients may be determined by a practitioner, an external device, and/or by the implantable device. More preferably, the matrix coefficients are previously determined and stored in a memory of the implantable device. It is understood that the matrix coefficients can be updated in the memory of the implantable device by an external programmer as a practitioner determines a change in the patient's clinical status.

In another embodiment, a plurality of given matrices of mixed data may be provided, along with means for selecting one of the plurality of given matrices to be applied in accordance with at least one criterion related to the patient's status. The criterion may be related to the patient's position, for example, determined by a sensor responsive to the patient's relative position to the analysis circuits of the implantable device.

In yet another embodiment, the implantable device includes means for analyzing a cardiac rhythm to classify tachyarrhythmias from the estimated atrial signals and a ventricular activity signal collected by the electrodes of the implantable device, and/or means for transmitting the estimated atrial activity signal to an external programmer. The external programmer preferably displays the estimated atrial activity signal on a display screen suitable for a practitioner to diagnose.

Advantageously, the use of a simple, standard medical device such as a known generator structure and a conventional monobody lead provides several benefits: minimum cost, fast and simple implantation procedure, minimizing the risk caused by implanting multiple leads.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

Figure 1:
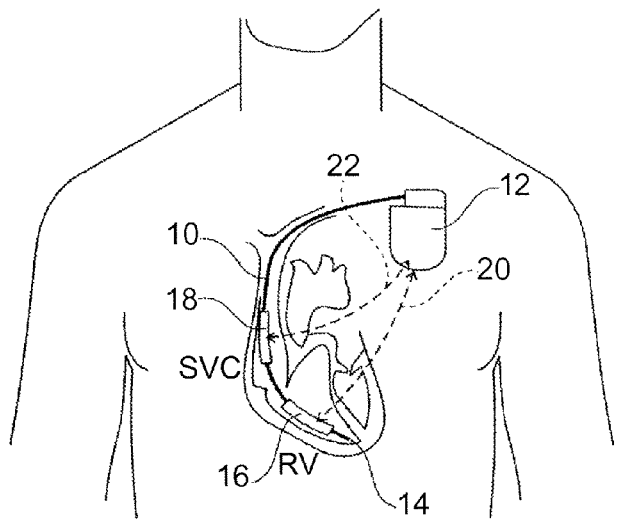
FIG. 1 is a schematic view of a single-chamber defibrillator implanted in a patient, with a dual coil monobody lead, in accordance with a preferred embodiment of the present invention.
Figure 2A:
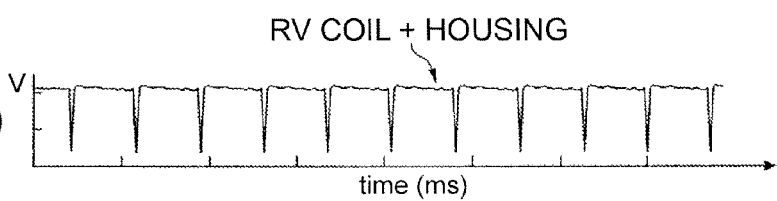
FIG. 2 shows representative examples of timing diagrams of the signals collected by the devices of FIG. 1, and of signals processed in accordance with present invention.
Figure 2B:
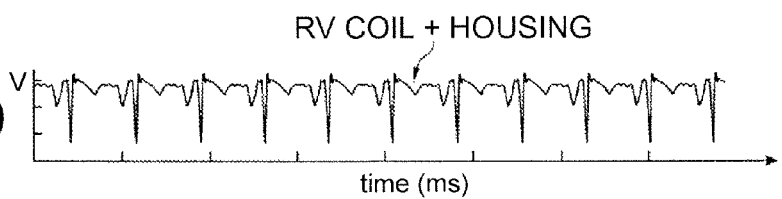
Figure 2C:
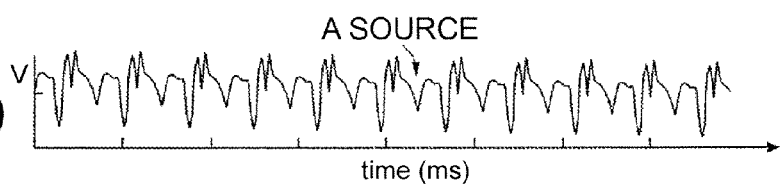
Figure 2D:
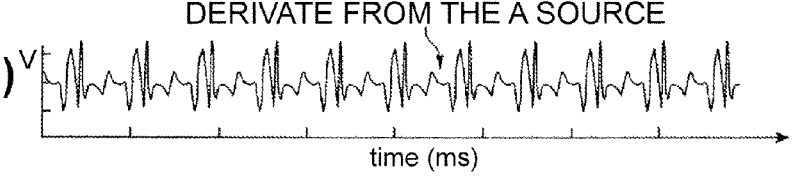
Figure 3:
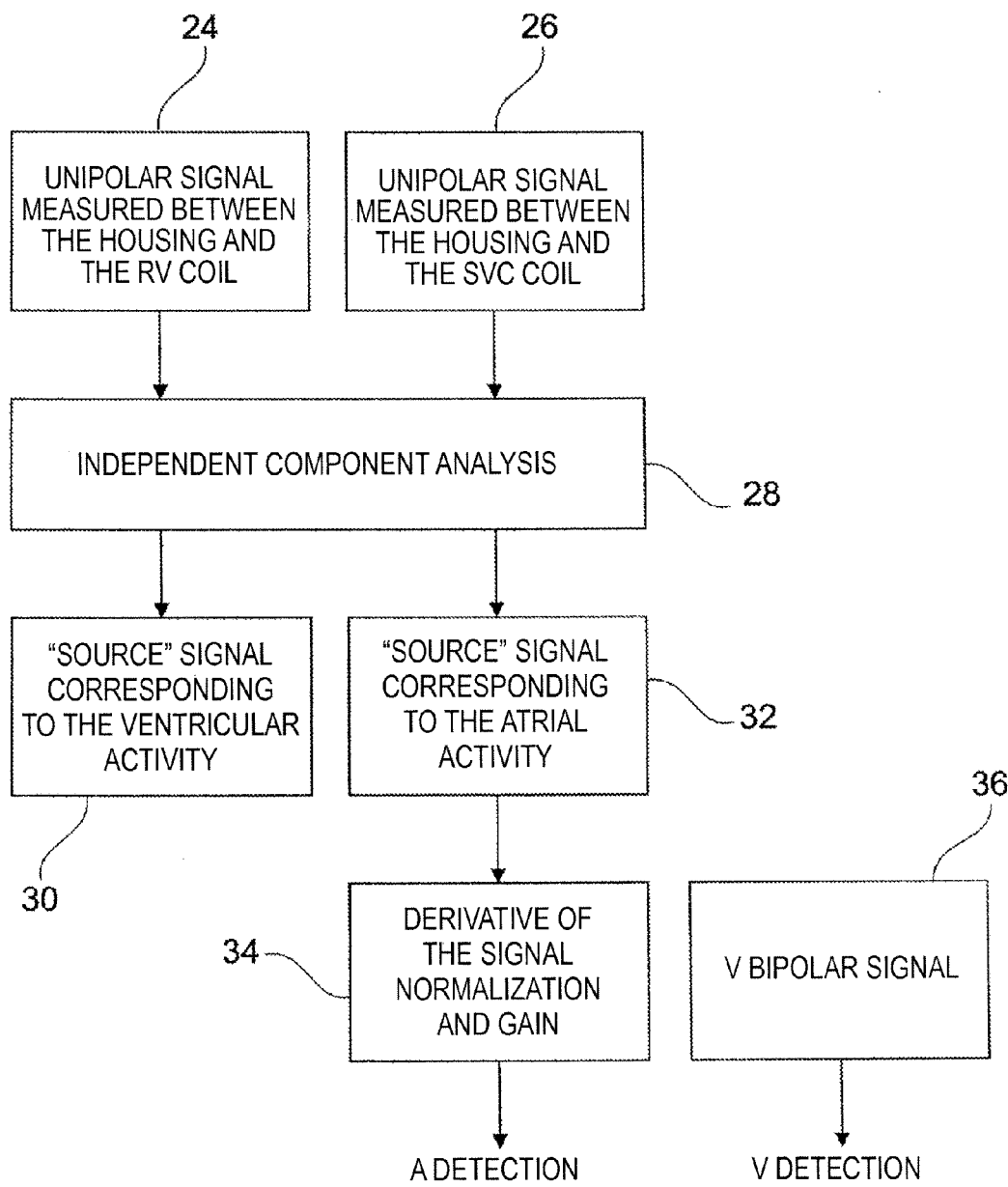
FIG. 3 is a flow chart illustrating a process for implementing the present invention.

With reference to FIGS. 1-3, various embodiments of the device and process according to the present invention will now be described.

In regards to its software aspects, the present technique for detecting atrial activity signal using a monobody lead can be implemented by an appropriate programming of a controlling software of a known device, for example, a cardiac pacemaker or a defibrillator/cardioverter, including hardware circuits and a control logic for collecting signals provided by endocardial leads and/or one or more implanted sensors. The present invention may particularly be applied to implantable devices such as those of the Ovatio or Paradym device families produced and marketed by Sorin CRM, Clamart France, formerly known as ELA Medical, Montrouge, France (Sorin Group).

A suitably implantable device such as those mentioned above includes a programmable microcontroller having a microprocessor to receive, format, and process electrical signals collected (detected) by implanted electrodes and to generate and deliver stimulation pulses to these electrodes. It is possible to transmit by telemetry software and store it in a memory of an implantable device, and execute the software to implement the functions and features of the present invention described herein. The adaptation of these implantable devices to implement the functions and features of the present invention is believed to be within the abilities of a person of ordinary skill in the art, and therefore will not be described in detail.

In FIG. 1, reference 10 designates a monobody lead, having a distal end that is inserted into a patient's venous network in both atrial and ventricular cavities to detect the cardiac activity and apply as required a shock. The lead 10 is provided at its proximal end with various connection elements to couple it to a generator 12, such as an implantable cardioverter/defibrillator, such as Paradym and Ovatio brand devices of Sorin CRM.

The lead 10 carries a distal electrode 14 for both detection and stimulation positioned at the apex of a right ventricular cavity. The lead 10 also includes on its distal end a first shock electrode coil 16 (hereinafter referred to as "RV" coil) placed in a right ventricle and forming, for example, a negative terminal for applying a shock for defibrillation, e.g., to a ventricle, more preferably to the right ventricle. The lead 10 also carries a second shock electrode coil 18 (hereinafter referred to as "SVC" coil) placed in the superior vena cava for applying a shock to the atrium.

One suitable monobody lead is, for example, the Isoline model manufactured by Sorin CRM, whose detailed structure is described in EP 1557194 A1 and its counterpart U.S. Patent Publication 2005/0177219, assigned to Sorin CRM, the disclosure of which is hereby incorporated by reference in its entirety. The present invention advantageously uses such a standard monobody lead to obtain a signal representative of the atrial activity (e.g., P waves), and an efficient discrimination of tachyarrhythmias by its origin, atrial or ventricular.

The SVC coil 18, located at or near the right atrium collects the atrial activity signal by monopolar detection between the SVC coil 18 and the metal housing (also referred to as a "case") of the generator 12.

The collected signal also includes the ventricular signal that is often of a larger amplitude than the atrial signal. The present invention operates to eliminate the ventricular contribution as much as possible, by performing an independent component analysis between the unipolar signal RV coil/housing (schematically shown in 20) and the monopolar signal SVC coil/housing (schematically shown in 22).

The independent component analysis (ICA) is a method of data analysis that operates a blind separation of signals from statistically independent sources. The ICA analysis is, for example, described in the book authored by Aapo Hyvarinen, Juha Karhunen and Erkki Oja, Independent Component Analysis, John Wiley & Sons, 2001, New York, to which reference is made for further details on its implementation.

The purpose of an ICA analysis is to identify a linear generative model represented by:

$$x = As,$$

where x is a vector of observed signals, s is a vector of source signals, and A is a matrix of mixing of the sources (also referred to as a "mixing matrix"). The ICA analysis assumes that each component of the vector $s = (s_1, s_2 \ldots s_n)$ is mutually independent. This assumption is adequate in the case where the atrial activity signal is independent of the ventricular activity signal because their sources are indeed independent, even if the collected signals contain both components.

The vector x is the vector of the observed first and second signals, i.e., SVC coil/housing signal 22 and RV coil/housing signal 20. These two signals are of the same nature (both monopolar signals), use the same reference potential (the housing as ground potential), and have comparable amplitudes (because of the substantially similar size of the electrodes being used). This facilitates the separation of the sources because the morphology of the different waves remains the same. These two observed signals are illustrated in the timing diagrams a) and b) in FIG. 2.

Referring to FIG. 3, the two signals, SVC coil/housing signal 22 and RV coil/housing signal 20 collected separately by the device (blocks 24 and 26) are subjected to the independent component analysis (block 28). The ICA analysis provides two separate components, namely a "source V" signal corresponding to the ventricular activity (block 30) and a "source A" signal corresponding to the atrial activity (block 32).

At this point, only the atrial source signal is of interest for the following steps. It is possible to directly collect a ventricular signal of good quality (block 36) via the distal electrode 14 located at the apex of the right ventricle.

The source signal corresponding to the atrial activity (i.e., source A), resulting from the ICA analysis, is shown on the timing diagram c) in FIG. 2.

Once the atrial source signal identified, it undergoes a transformation (block 34) via, for example, a derivative operation conducted in software to determine a vector of differences between two successive sample points and to reconstruct P-waves that are more similar to the real P waves collected in a bipolar signal.

The result after transformation is shown on the timing diagram d) of FIG. 2. This transformation by the derivation operation also allows the atrial source signal not to be reduced or degraded by the various filters and pre-processing that are applied to signals collected by a conventional defibrillator.

In a preferred embodiment, to the extent that there is an uncertainty with respect to the magnitude of the sources obtained by the ICA analysis, the derivative signal may be normalized so that its maximum absolute value is made equal to unity.

In addition, the implantable device may apply an adequate gain (i.e., amplification) to the estimated signal thus derived and normalized so that the detection of P waves is done with a sensitivity similar to that of conventional dual-chamber devices, for example, a gain value of about 20.

The technique in accordance with the foregoing embodiment of the present invention was tested with fifteen patients by collecting and analyzing signals about twenty seconds long. It produced good results showing a clear improvement in the detection of P waves as compared to a conventional technique of atrial detection that does not process the SVC coil/housing signal 22.

In one embodiment of the present invention, the atrial source signal collected and processed as described above may be used in combination with the ventricular detection signal collected by the distal electrode 14, to perform a rhythm analysis to enable a classification of tachyarrhythmias.

This tachyarrhythmia analysis is, for example, performed using the PARAD, PARAD+ or STABILITY+ algorithms described in EP 0 626 182 A1 and its counterpart U.S. Pat. No. 5,462,060, EP 0 838 235 A1 and its counterpart U.S. Pat. No. 5,868,793, EP 0 813 888 A1 and its counterpart U.S. Pat. No. 5,891,170 and EP 1 208 873 A1 and its counterpart U.S. Pat. No. 6,889,080 (all in the name of Sorin CRM, previously known as ELA Medical, Sorin Group), the disclosures of which are incorporated herein by reference.

In one embodiment of the present invention, the atrial source signal collected and processed according to the present invention is used as a diagnostic tool for a physician, for example, by displaying the derived signal on a display screen of an external programmer.

In an alternative embodiment, where, for example, the calculations required by ICA analysis are too complex to be performed in real time by the microcontroller of the generator 12, the coefficients of a mixing matrix may be calculated during a preliminary learning phase, for example, during a patient follow-up session, and stored in a memory in the implantable device. In this way, the implantable device applies the predetermined mixing matrix coefficients in real time.

In yet another embodiment, coefficients for several mixing matrices, corresponding to different situations, may be calculated. For example, matrix coefficients may be calculated for a patient being in two different physical positions, such as in a lying down position and in a standing up position, each of which corresponds to different positions of the SVC and RV coils in the myocardium, and leads to significantly different morphology signals.

The implantable device in this embodiment selects the appropriate matrix coefficients according to the situation appropriate at the time of the ICA analysis. The position of the patient may be determined and used by the implantable device to select an appropriate set of matrix coefficients for the ICA analysis. The patient's position may be determined in any manner known. For example, the position of the patient can be determined in a known manner by an analysis of the patient's cardiac electrogram. See, e.g., EP 278,864 (assigned to Sorin CRM), which describes such a position determination, which disclosure is incorporated herein by reference. Alternately, a sensor can be used, e.g., a three dimensional accelerometer, for determining the patient's position, as described in Igarashi, "*Integrated Microsized Semiconductor Strain Gauge And Its Biomedical Applications,*" *Implantable sensors for closed-loop prosthetic systems*, Chapter 6, (Futura Publishing Company Inc., 1985; edited by Wen H. Ko and co-edited by Jacques Mugica & Alain Ripart).

One skilled in the art will appreciate that the present invention can be practiced by other than the embodiments described above, which are provided for purposes of illustration and not of limitation.

The invention claimed is:

1. An active implantable medical device for estimating an atrial activity signal representative of a patient's atrial depolarization activity, comprising:
   a monobody lead comprising:
      a ventricular coil forming both a first shock electrode and a first detection electrode, wherein the first detection electrode is configured to detect depolarization signals from a ventricle of the patient;
      a supraventricular coil forming both a second shock electrode and a second detection electrode, wherein the second detection electrode is configured to detect depolarization signals from a superior vena cava of the patient; and
      a distal electrode comprising a third detection electrode, wherein the third detection electrode is configured to detect depolarization signals from the ventricle; and
   a generator comprising:
      a housing forming a metal reference potential electrode; and
      circuitry configured to:
         analyze the depolarization signals collected by said first, second and third detection electrodes,
         deliver an antitachycardia shock to the patient's ventricle,
         collect a first unipolar signal between the ventricular coil and the housing of the generator,
         collect a second unipolar signal between the supraventricular coil and the housing of the generator,
         perform an Independent Component Analysis (ICA) on said first and second unipolar signals, and
         determine, based on said Independent Component Analysis (ICA) performed on said first and second unipolar signals, an estimated atrial activity signal.

2. The device of claim 1, wherein said circuitry is further configured for normalizing said estimated atrial activity signal to a predetermined maximum absolute value.

3. The device of claim 1, wherein said circuitry is further configured for transforming said estimated atrial activity signal by a derivative operation.

4. The device of claim 3, wherein said circuitry is further configured for normalizing said estimated atrial activity signal to a predetermined maximum absolute value.

5. The device of claim 4, wherein said circuitry is further configured for applying a predetermined gain to said estimated atrial activity signal after normalization.

6. The device of claim 1, wherein said circuitry is further configured for operating the ICA from a given mixing matrix having a set of matrix coefficients, and said generator further comprising a memory storing said set of matrix coefficients.

7. The device of claim 6, wherein said circuitry is further configured for operating the ICA by identifying a linear generative model represented by a vector of said first and second unipolar signals being equal to a product of said mixing matrix and a vector of source signals, the vector of source signals corresponding to a ventricular depolarization activity of the patient and said atrial depolarization activity of the patient.

8. The device of claim 1, wherein said circuitry is further configured for providing a plurality of given mixing matrices, and selecting one of the plurality of given mixing matrices to be applied in accordance with at least one criterion of a patient's status determined by said analyzing the depolarization signals.

9. The device of claim 8, wherein said criterion for patient's status is a position of the patient.

10. The device of claim 9, further comprising a sensor having an output corresponding to the position of the patient.

11. The device of claim 8, further comprising a sensor responsive to a relative position of the patient to said circuitry, wherein said at least one criterion of the patient's status being related to the patient's position.

12. The device of claim 1, wherein said circuitry is further configured for analyzing a rhythm and classifying tachyarrhythmias from said estimated atrial activity signal and from a ventricular activity signal collected between the distal electrode and the housing of the generator.

13. The device of claim 1, wherein said circuitry is further configured for transmitting said estimated atrial activity signal to an external programmer having a display screen, where said estimated atrial activity signal is displayed on said display screen of the external programmer.

14. A method comprising:
   detecting depolarization signals from a ventricle of a patient using a ventricular coil;
   detecting depolarization signals from a superior vena cava of the patient using a supraventricular coil;
   analyzing the depolarization signals collected using the ventricular coil and the supraventricular coil;
   delivering an antitachycardia shock to the ventricle;
   collecting a first unipolar signal between the ventricular coil and a housing of a generator, wherein the housing comprises a metal reference potential electrode;
   collecting a second unipolar signal between the supraventricular coil and the housing of the generator;
   performing an Independent Component Analysis (ICA) on the first and second unipolar signals; and
   determining, based on the Independent Component Analysis (ICA) performed on the first and second unipolar signals, an estimated atrial activity signal.

15. The method of claim 14, further comprising transforming said estimated atrial activity signal by a derivative operation.

16. The method of claim 15, further comprising normalizing said estimated atrial activity signal to a predetermined maximum absolute value.

17. The method of claim 16, further comprising applying a predetermined gain to said estimated atrial activity signal after normalization.

18. The method of claim 14, further comprising:
   operating the ICA from a given mixing matrix having a set of matrix coefficients; and
   storing said set of matrix coefficients in a memory.

19. The method of claim 14, further comprising analyzing a rhythm and classifying tachyarrhythmias from said estimated atrial activity signal and from a ventricular activity signal collected between a distal electrode and the housing of the generator.

20. A generator of an implantable medical device, comprising:
   a housing comprising a metal reference potential electrode; and
   a circuit configured to:
      receive a plurality of depolarization signals collected by a plurality of electrodes from a ventricle and a superior vena cava of a patient, the plurality of electrodes comprising a ventricular electrode configured to collect depolarization signals from the ventricle and a supraventricular electrode configured to collect depolarization signals from the superior vena cava,
      analyze the depolarization signals,
      deliver an antitachycardia shock to the ventricle,
      collect a first unipolar signal between the ventricular electrode and the housing,
      collect a second unipolar signal between the supraventricular electrode and the housing,
      perform an Independent Component Analysis (ICA) on the first and second unipolar signals, and
      determine, based on said Independent Component Analysis (ICA) performed on the first and second unipolar signals, an estimated atrial activity signal.

* * * * *